United States Patent [19]
Krenitsky et al.

[11] Patent Number: 4,780,452
[45] Date of Patent: Oct. 25, 1988

[54] F-SUBSTITUTED-3-β-D-RIBOFURANOSYL-3H-IMIDAZO[4,5-B]PYRIDINES AND PHARMACEUTICAL COMPOSITIONS THEREOF

[75] Inventors: Thomas A. Krenitsky, Chapel Hill; Janet L. Rideout, Raleigh; George W. Koszalka, Apex, all of N.C.

[73] Assignee: Burroughs Wellcome Co., Research Triangle Park, N.C.

[21] Appl. No.: 905,243

[22] Filed: Sep. 8, 1986

[51] Int. Cl.$^4$ .................. A61K 31/70; C07H 17/02
[52] U.S. Cl. .......................... 514/45; 514/46; 514/49; 514/50; 536/23; 536/24; 536/26
[58] Field of Search .............. 514/42, 45; 536/24, 536/28

[56] References Cited
U.S. PATENT DOCUMENTS
4,309,419  1/1982  Wolberg et al. ............... 536/24
4,322,411  3/1982  Vinegar et al. ............... 536/24

OTHER PUBLICATIONS
Gupta et al., Indian J. of Chemistry, vol. 20B (9), pp. 817-819, 1981.

Primary Examiner—J. R. Brown
Assistant Examiner—L. Eric Crane
Attorney, Agent, or Firm—Donald Brown

[57] ABSTRACT

This invention discloses a group of compounds of formula (I)

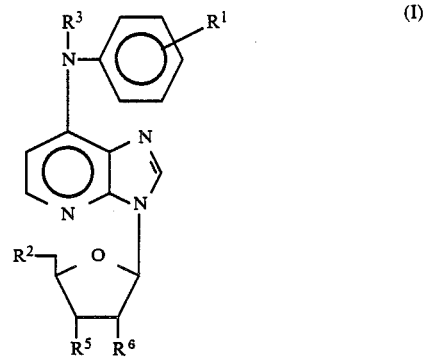

wherein $R^1$ is hydrogen, halo, $C_{1-4}$ alkyl, $C_{1-4}$ alkoxy, $COOR^4$ ($R^4$ is H or $C_{1-4}$ alkyl) or trifluoromethyl; $R^2$, $R^5$ and $R^6$ are the same or different and can be hydrogen, hydroxy, $OCOR^7$ (wherein $R^7$ is hydrogen, $C_{1-4}$ alkyl, phenyl optionally substituted) or halo; and $R^3$ is hydrogen, $COR^4$, $C_{3-6}$ cycloalkyl or $C_{1-4}$ alkyl or alkenyl; $R^2$ may also be a phosphate group and pharmaceutically acceptable salts thereof which have been found to have analgesic activity. In addition, these compounds have antiinflammatory, antipyretic, antihypertensive and vasodilatory activity in varying degrees. Some of these compounds also have antiprotozoal and antiviral properties.

13 Claims, No Drawings

F-SUBSTITUTED-3-β-D-RIBOFURANOSYL-3H-IMIDAZO[4,5-B]PYRIDINES AND PHARMACEUTICAL COMPOSITIONS THEREOF

This invention relates to compounds useful in medicine, to the synthesis of these compounds, to pharmaceutical formulations containing the compounds and the preparation of such formulations, and to the use of the compounds in medical practice.

The compounds of formula (I),

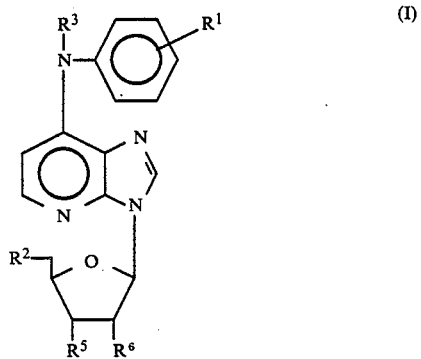

wherein $R^1$ is hydrogen, halo, $C_{1-4}$ alkyl, $C_{1-4}$ alkoxy, $LCOOR^4$ ($R^4$ is H or $C_{1-4}$ alkyl) or trifluoromethyl; $R^2$, $R^5$ and $R^6$ are the same or different and can be hydrogen, hydroxy, $OCOR^7$ (wherein $R^7$ is hydrogen, $C_{1-4}$ alkyl, phenyl optionally substituted) or halo; and $R^3$ is hydrogen, $COR^4$, $C_{3-6}$ cycloalkyl or $C_{1-4}$ alkyl or alkenyl; $R^2$ may also be a phosphate group and pharmaceutically acceptable salts thereof have been found to have analgesic activity. In addition, these compounds have antiinflammatory, antipyretic, antihypertensive and vasodilatory activity in varying degrees. Some of these compounds also have antiprotozoal and antiviral properties.

Of the compounds of formula (I) those of formula (IA)

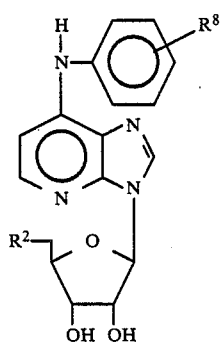

wherein $R^8$ is hydrogen or halo and $R^2$ is as in formula (I) are preferred.

The most preferred compounds as anti-inflammatory and/or analgesic agents are

A. 7-Anilino-3-β-D-ribofuranosyl-3H-imidazo[4,5-b]pyridine

B. 7-Anilino-3-(5-chloro-5-deoxy-β-D-ribofuranosyl)-3H-imidazo[4,5-b]pyridine

C. 7-Anilino-3-(5-deoxy-β-D-ribofuranosyl))-3H-imidazo[4,5-b]pyridine

D. 7-Anilino-3-(5-fluoro-5-deoxy-β-D-ribofuranosyl)-3H-imidazo[4,5-b]pyridine

The compounds of formula (I) have the analgesic, acute antiinflammatory and antipyretic activities of acetaminophen and arachidonate cyclooxygenase (AACO) inhibitors. However, formula (I) compounds do not inhibit AACO in vitro or ex vivo. They do not produce the gastric and platelet damage associated with administration of AACO inhibitors.

The compounds of formula (I) may be used in the relief, treatment or prophylaxis of pain, i.e., as an analgesic, of inflammation or of fever, i.e., as an antipyretic, in a mammal, including man, such as that resulting from headache, toothache, pain following general dental procedures, oral and general surgery, dysmenorrhea, myalgia, pain of unresectable cancer, joint and peripheral nerve disorders, rheumatoid arthritis, rheumatoid spondylitis, osteoarthritis, gouty arthritis and other arthritic conditions, pyresis and other conditions associated with pain, inflammation and fever. They can also be used to treat hypertensive conditions and congestive heart failure.

The amount of the active compound, i.e., a compound of formula (I), required for use in the above conditions will, of course, vary with the route of administration, the specific compound of formula (I), the condition under treatment, and the mammal undergoing treatment, and is ultimately at the discretion of the physician or veterinarian. However, a suitable analgesic dose of the active compound for a mammal is in the range of from 0.01 to 1.00 mg per kilogram body weight per day; preferably in the range of 0.02 to 0.20 mg/kg; a typical dose for a human recipient being 0.10 mg/kg body weight per day.

The desired dose is preferably presented as in the range of from two to four subdoses administered at appropriate intervals throughout the day. Thus where three sub-doses are employed each will lie in the range of from, 0.0033 to 0.33 mg/kg body weight, a typical dose for a human recipient being 0.033 mg/kg body weight. The anti-inflammatory, antipyretic and the antihypertensive doses are in the same range of the analgesic dose.

While it is possible for a compound of formula (I), active compound, to be administered alone as the raw chemical, it is preferable to present the active compound as a pharmaceutical formulation. Formulations of the present invention, both for veterinary and for human medical use, comprise an active compound together with one or more pharmaceutically acceptable carriers thereof and optionally any other therapeutic ingredients. The carrier(s) must be pharmaceutically acceptable in the sense of being compatible with the other ingredients of the formulation and not deleterious to the recipient thereof. The other therapeutic ingredient(s) may include other analgesics (especially those that are centrally acting, e.g., codeine), other anti-inflammatories, other antipyretics, or other antihypertensives.

The formulations include those suitable for oral, rectal, topically or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulation.

Formulation of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or molding, optionally with one or more accessory ingredients. Compressed tablets may be prepared by compressing, in a suitable machine, the active compound being in a free-flowing form such as a powder or granules, optionally mixed with a binder, lubricant, inert diluent, surface active or dispersing agent. Molded tablets may be made by molding in a suitable machine, comprising a mixture of the powdered active compound with any suitable carrier.

A syrup may be made by adding the active compound to a concentrated, aqueous solution of a sugar, for example sucrose, to which may also be added any accessory ingredient. Such accessory ingredient(s) may include flavorings, an agent to retard crystallization of the sugar or an agent to increase the solubility of any other ingredient, such as polyhydric alcohol, for example, glycerol or sorbitol.

Formulations for rectal administration may be presented as a suppository with a usual carrier such as cocoa butter.

Formulations suitable for parenteral administration conveniently comprise a sterile aqueous preparation of the active compound which is preferably isotonic with the blood of the recipient.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

Compounds of formula (I) may be prepared enzymatically by reacting compounds of formula (II) with a suitable ribofuranosyl or ribofuranosyl derivative donor in the presence of the appropriate enzymes.

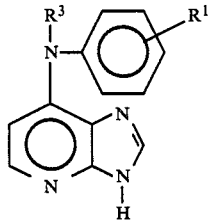

(II)

Such enzymatic processes include the preparation of compounds of formula (I) from the appropriate free base using phosphorylase-type enzymes in a manner known in the art: see, for instance, T. A. Krenitsky, G. B. Elion, R. A. Strelitz, G. H. Hitchings, *J. Biol. Chem.*, 242, 2675–2682, (1967), U.S. Pat. No. 4,347,315, and U.S. Pat. No. 4,381,344.

Alternatively, the enzymatic process may be accomplished by microbiological processes such as that disclosed in German Offenlegungsschrift No. 2 209 078 wherein Q is hydrogen and the riboside donor system comprises bacteria of the genera Brevibacterium, Arthrobacter, Corynebacterium or Micrococcus and the culture medium which includes glucose.

Whenever the compound of formula (I) is required to carry acyloxy groups for $R^2$, $R^5$ and $R^6$, a corresponding starting compound having hydroxy groups in these positions is reacted with acylating agents such as acetic anhydride or benzoyl chloride according to conventional methods. Acylation in many cases may be effected before or after other synthetic steps.

In turn, compounds of formula (II) may be made by reacting the compound of formula (III) with an amine of formula (IV) at elevated pressure and temperature as required.

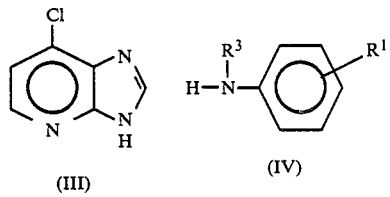

(III)                (IV)

The compound of formula (III) can be made by reacting the N-oxide of the compound of formula (V), i.e., VA, with $POCl_3$. The N-oxide of formula (VA) is made from the compound of formula (V) by treatment with hydrogen peroxide or m-chloroperbenzoic in acetic acid, trifluoroacetic acid, a chlorinated solvent or a solvent mixture such as acetic acid and methylene chloride.

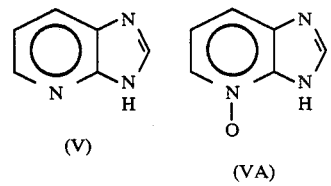

(V)                (VA)

The compound of formula (VI) can be condensed with ethyl orthoformate under acidic conditions to yield the compound of formula (V).

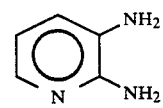

(VI)

Compounds of formula I can be synthesized chemically by the reaction of an excess of an aniline, generally 3 or more equivalents, with 7-chloro-3-β-D-ribofuranosyl-3H-imidazo[4,5-b]pyridine in an appropriate solvent, such as water, in a flask or pressure vessel at elevated temperatures such as between 100° to 160° C. The 7-chloro-3-β-D-ribofuranosyl-3H-imidazo[4,5-b]pyridine may be prepared by the enzymatic process taught herein or by methods taught in the art. (T. Itoh, T. Sugawara and Y. Mizuno, *Nucleosides and Nucleotides*, 1, 179–190 (1980); K. B. de Roos and C. A. Salemink, *Rec. trav. chim.* 90, 654–662 (1971); J. A. Montgomery and K. Hewson, *J. Med. Chem.*, 9 354–357 (1966)).

Another chemical method involves the use of 5,7-dichloro-3-β-D-ribofuranosyl-3H-imidazo[4,5-b]pyridine which is synthesized by the enzymatic method taught herein or by a method known in the art. (T. Itoh, T. Sugarawa, A. Nomura and Y. Mizuno, *Nucleotides and Nucleosides*, 2, 387–397 (1983)); J. E. Schelling and C. A. Salemink, *Rec. trav. chim.*, 91 650–656 (1972); Ibid., 94, 153–156 (1975); B. L. Cline, R. P. Panzica and L. B. Townsend, *J. Heterochem.*, 15, 839–847 (1978)) or as in Example 12. The 7-chloro moiety is replaced by an anilino group through reaction at high temperature (130°–180° C.) in an appropriate solvent. Alternatively, a 2′,3′,5′-tri-O-acetylated derivative of this nucleoside can be reacted with the aniline and any remaining acyl group removed by hydrolysis by methods known in the art, e.g., methanolic ammonia or alkoxide at low temperature. The 5-chloro substituent is removed reductively, for example, by hydrogenolysis using palladium on charcoal and hydrogen gas.

An additional method of synthesis involves the use of 5-chloro-7-anilino-3H-imidazo[4,5-b]pyridine. Fusion of this heterocycle with a nucleoside precursor, such as 1,2,3,5-tetra-O-acetyl-β-D-ribofuranose or 1-O-acetyl-2,3,5-tri-O-benzoyl-β-D-ribofuranose gives the acylated derivative. The acyl groups and the 5-halo substituent are removed as mentioned above. Alternatively, the disubstituted nucleoside can be synthesized by the enzymatic method taught herein and the 5-halo substituent removed reductively.

When $R_2$ of the compound of formula (I) is a phosphate group, this may be introduced into the corresponding compound having a hydroxyl group in that position by phosphorylation using traditional phosphorylating agents such as trialkyl phosphates, e.g., triethyl phosphate, with a phosphorus oxyhalide such as phosphoryl chloride. When this technique is used it is advantageous to block the 2′- and 3′-positions of the ribose moiety either by blocking only these two positions by using appropriate conditions or by blocking the 2′-, 3′- and 5′-positions and then selectively deblocking the 5′ position. The latter course may be facilitated by first blocking the 5′ position with a bulky group, such as a trityl group or a t-butyldimethylsilyl group, then blocking the 2′- and 3′-positions by conventional means, and finally deblocking the 5′-position. After phosphorylation the 2′- and 3′-positions are then deblocked to afford the required compound.

Rather than block the 2′- and 3′-positions as described above, it is preferred to use phosphoryl chloride in the presence of a trialkylphosphate (preferably triethyl phosphate) and a trace of water at a temperature of about 0° C. or below. This forms the 5′-phosphoro dichloridate which is then hydrolysed to the 5′-phosphate upon treatment with water at slightly basic pH.

Salts of phosphate-substituted compounds of formula (I) are obtained by conventional reactions between the phosphate derivative and an appropriate base in aqueous media.

When used in medicine, the salts of a compound of formula (I) should be both pharmacologically and pharmaceutically acceptable, but non-pharmaceutically acceptable salt may conveniently be used to prepare the free active compound or pharmaceutically acceptable salts thereof and are not excluded from the scope of this invention.

Such pharmacologically and pharmaceutically acceptable salts include, but are not limited to, those prepared from the following acids: hydrochloric, hydrobromic, sulfuric, nitric, phosphoric, salicylic, p-toluenesulfonic, tartaric, citric, methanesulfonic, maleic, formic, malonic, succinic isethionic, lactobionic, naphthalene-2-sulfonic, ethanesulfonic, sulfamic and benzenesulfonic.

The following Examples are provided by the way of illustration of the present invention and should in no way be construed as a limitation thereof. All temperatures indicated are in degrees Celsius.

EXAMPLE 1

7-Anilino-3-β-D-ribofuranosyl-3H-imidazo[4,5-b]pyridine

Uridine (50 mmoles, 12.3 g) and 7-anilino-3H-imidazo[4,5-b]pyridine (33 mmole, 7.0 g), were suspended in 65 mL of 7.6 mM $K_xH_xPO_4$, pH 8.0. After stirring, the pH of this suspension was adjusted from pH 6.6 to 7.4 with potassium hydroxide. The enzyme catalysts purified from *Escherichia coli*, purine nucleoside phosphorylase (13,000 I.U.) and uridine phosphorylase (335 I.U.) (Krenitsky et al., *Biochemistry*, 20, 3615, 1981 and U.S. Pat. No. 4,381,344) were then added and the suspension stirred at 38° C. for 5 days. The reaction mixture was filtered. The solids were washed with water and suspended in 250 mL of methanol, brought to a boil, and filtered while hot. The filtrate was dried and extracted with water at room temperature. The product in the washed solids was further purified by several recrystallizations from boiling water. Analytically pure 7-anilino-3-β-D-ribofuranosyl-3H-imidazo[4,5-b]pyridine (30 mmole, 10.46 g), m.p. 189° C. was obtained representing a yield of 91% with respect to the amount of 7-anilino-3H-imidazo[4,5-b]pyridine base used.

Anal. Calcd. for $C_{17}H_{18}N_4O_4$: C, 59.64; H, 5.30; N, 16.36. Found: C, 59.60; H, 5.34; N, 16.33.

EXAMPLE 2

7-Anilino-3H-imidazo[4,5-b]pyridine

Method A:

To 7-chloro-3H-imidazo(4,5-b)pyridine (16 g, 97 mmol) was added aniline (200 mL, 2.1 mol). The resulting mixture was heated under a nitrogen atmosphere at 130° C. for 24 hours. Benzene was added to the cooled mixture and the precipitate was filtered. The solid was dissolved in water and 1N NaOH was added to give a pH reading of 9. The precipitate was filtered and recrystallized from EtOH (decolorized by charcoal) to give 7.2 g (35%) of the 7-anilino-3H-imidazo[4,5-b]pyridine, m.p. 251°–252° C.

Anal. Calcd. for $C_{12}H_{10}N_4$: C, 68.56; H, 4.79; N, 26.65. Found: C, 68.50 H, 4.81; N, 26.62.

Method B:

A mixture of 7-chloro-3H-imidazo[4,5-b]pyridine hydrate (20 g, 117 mmol), aniline (11.5 g, 124 mmol) and p-toluenesulfonic acid hydrate (0.5 g, 2.6 mmol) in 300 mL of water was heated at reflux for 24 hours. The solution was evaporated under reduced pressure to dryness. The residue was suspended in water and 1N NaOH was added to give a pH reading of 9. Filtration and washing the precipitate with water gave 24.5 g (98.5%) of the product, m.p. 249°–250° C.

Anal. Calcd. for $C_{12}H_{10}N_4$ 1/6$H_2O$: C, 67.59; H, 4.89; N, 26.28. Found: C, 67.60; H, 4.78; N, 26.50.

EXAMPLE 3

7-(2-Chloroanilino)-3-β-D-ribofuranosyl-3H-imidazo[4,5-b]pyridine 7-(2-Chloroanilino)-3H-imidazo[4,5-b]pyiridine. 0.5HCl (0.19 g, 0.47 mmol) was added to 7.5 mL bis(2-methoxyethyl)ether and heated at 100° C. for 10 min then cooled to room temperature. An aqueous solution (10 mL) of uridine (0.7 g, 2.87 mmol) was added and the pH adjusted to 7.5 with concentrated ammonium hydroxide. Purine nucleoside phosphorylase (4135 units), uridine phosphorylase (1140 units), and $K_xH_xPO_4$ (0.28 mmol, pH 7.0) in 2.8 mL water were combined with the aqueous-ether solution. After 3 days at 35° C., the reaction mixture was filtered and the filtrate applied to a column packed with an anion exchange resin (AG-1 (OH$^-$); 2.5×7 cm) that had been preequilibrated with a mixture of water and methanol (70/30; v/v). The product was eluted with this solvent mixture and had an $R_f$ value of 0.47 on TLC (cellulose/$H_2O$). After removal of the solvent in vacuo, the product was dissolved in 15 mL of a n-propanol/water mixture (30/70; v/v) and chromatographed using a column packed with polyacrylamide gel (P-2) (2.5×90 cm) that had been equilibrated with the n-propanol/water mixture. After elution of the product with this mixture and removal of the solvents, 0.163 mg of 7-(2-chloroanilino)-3-β-D-ribofuranosyl-3H-imidazo[4,5-b]pyridine as a half hydrate was obtained, m.p. 135° C.

Anal. Calcd. for $C_{17}H_{17}ClN_4O_4.\frac{1}{2}H_2O$; C, 52.92; H, 4.70; N, 14.52; Cl, 9.19. Found: C, 53.10; H, 4.73; N, 14.52; Cl, 9.19.

EXAMPLE 4

7-(3-Chloroanilino)-3-β-D-ribofuranosyl-3H-imidazo[4,5-b]pyridine

An aqueous suspension (10 mL) containing 7-(3-chloroanilino)-3H-imidazo(4,5-b)pyridine (0.7 g, 2.86 mmol), prepared by the method of Example 2, uridine (1.05 g, 4.29 mmol) and $K_xH_xPO_4$ (0.1 mmol) was adjusted to pH 7.2 with KOH. Uridine phosphorylase (360 units) and purine nucleoside phosphorylase (800 units) were then added as in Example 2. The reaction temperature was maintained at 37° C.

An additional 1000 units of purine nucleoside phosphorylase were added on day 7, followed by the addition of 900 units uridine phosphorylase and 1000 units of purine nucleoside phosphorylase on day 13. On day 13, 2 mmol (0.5 g) of uridine was added. The volume of the reaction was increased on day 19 by the addition of 50 mL of $K_xH_xPO_4$ (0.5 mmol, pH 7.0). Bis(2-methoxyethyl)ether (50 mL) was added on day 23, and the pH was adjusted to 7.1 with acetic acid. After an additional three days at 37° C., the reaction mixture was filtered. The precipitate was dissolved in 165 mL of an n-propanol/water mixture (30/70; v/v) and applied to an AG-1(OH$^-$) column (2.5×7.5 cm) which was pre-equilibrated with a mixture of water and methanol (10/90; v/v). The product was eluted with this solvent. The reaction mixture filtrate was treated in an identical manner after the addition of 50mL methanol. The eluates were combined and dried in vacuo. The resulting solid was dissolved in 35 mL of a n-propanol/water mixture (30/70; v/v) and applied to a column packed with polyacrylamide gel (P-2) (5×90 cm) that had been equilibrated with the mixture of n-propanol and water. After elution and removal of the solvents, 0.371 g of 7-(2-chloroanilino)-3-β-D-ribofuranosyl-3H-imidazo[4,5-b]pyridine was obtained, m.p. 207° C.

Anal. Calcd. for $C_{17}H_{17}ClN_4O_4$; C, 54.19; H, 4.55; N, 14.87; Cl, 9.41. Found: C, 54.12; H, 4.56; N, 14.83; Cl, 9.49.

EXAMPLE 5

7-(4-Chloroanilino)-3-β-D-ribofuranosyl-3H-imidazo[4,5-b]pyridine 7-(4-Chloroanilino)-3H-imidazo[4,5b]pyridine (0.77 g, 3.16 mmol) prepared by the method of Example 2, and uridine (2.5 g, 10 25 mmol) were dissolved in 70 mL bis(2-methoxyethyl)ether. This solution was added to an aqueous solution (130 mL) of $K_xH_xPO_4$(1.3 mmol, pH 7.4). Uridine phosphorylase (950 units) and purine nucleoside phosphorylase (900 units) were then added as in Example 2 and the temperature maintained at 37+ C. with constant stirring. After 14 days the reaction mixture was filtered and the filtrate applied to an AG-1(OH$^-$) column (2.5×13 cm) which was pre-equilibrated with a mixture of water and methanol (70/30; v/v). The product was eluted with this solvent. After evaporation of the solvents in vacuo, the product was was dissolved in a mixture of water and n-propanol (70/30, v/v) and chromatographed on polyacrylamide gel (P-2). Fractions which contained only product by TLC on cellulose in water ($R_f$=0.17) were combined and the solvent removed in vacuo yielding 0.564 g of 7-(4-chloroanilino)-3β-D-ribofuranosyl-3H-imidazo[4,5-b]pyridine. The yield was 46.9%, m.p. 215° C.

Anal. Calcd. for $C_{17}H_{17}ClN_4O_4$: C, 54.19; H, 4.55; N, 14.87; Cl, 9.41. Found: C, 54.35; H, 4.76; N, 14.62; Cl, 9.30.

EXAMPLE 6

7-anilino-3-(5-chloro-5-deoxy-β-D-ribofuranosyl)-3H-imidazo[4,5-b]pyridine

7-Anilino-3H-imidazo[4,5-b]pyridine (0.8 g, 3.7 mmol) and 5'-chloro-5'-deoxyuridine (15 g, 5.7 mmol) were combined in 10 mL of 10 mM $K_xH_xPO_4$, pH 7.4. Uridine phosphorylase (315 units) and purine nucleoside phosphorylase (1800 units) previously purified from *E. coli*, were added and the reaction stirred at 35° C. After 4 days an additional 84 units of uridine phosphorylase and 100 mL phosphate buffer were added. Twenty-one days later the particulates were collected by filtration and recrystallized from boiling ethanol yielding 0.982 g of 72% of 7-anilino-3-(5-chloro-5-deoxy-β-D-ribofuranosyl)-3H-imidazo[4,5-b]pyridine, m.p. 195° C. (dec.):

Anal. Calcd. for $C_{17}H_{17}ClN_4O_3$: C, 56.33; H, 5.25 N, 14.60. Found: C, 56.20; H, 5.21; N, 14.50.

EXAMPLE 7

7-Anilino-3-(5-deoxy-β-D-ribofuranosyl)-3H-imidazo[4,5-b]pyridine

7-Anilino-3H-imidazo[4,5-b]pyridine (0.8 g, 3.77 mmol) and 5'-deoxyuridine (2 g, 0.87 mmol) were added to a 10 mL solution of 10 mM $K_xH_xPO_4$, pH 7.4 and 0.04% potassium azide. After mixing, 180 units of uridine phosphorylase and 1800 units of purine nucleoside phosphorylase were added. The reaction was continuously mixed at 35° C. for 6 days. Solids were collected by filtration and recrystallized from boiling ethanol yielding 0.943 g of the 7-anilino-3-(5-deoxy-β-D- ribofuranosyl)-3H-imidazo[4,5-b]pyridine. This corresponded to a yield of 77%; m.p. 219° C.

Anal. Calcd. $C_{17}H_{18}N_4O_3$: C, 62.57; H, 5.56; N, 17.17. Found: C, 62.43; H, 5.60; N, 17.12.

EXAMPLE 8

7-Anilino-3-β-D-ribofuranosyl)-3H-imidazo[4,5-b]pyridine a.

7-Chloro-3-β-D-ribofuranosyl)-3H-imidazo[4,5-b]pyridine

7-Chloro-3H-imidazo[4,5]pyridine (0.013 mole, 2 g) and uridine (0.014 mole, 3.4 g), were suspended in 32.3 ml of 0.01M potassium phosphate, pH 7.4. The enzyme catalysts purine nucleoside phosphorylase (970 units) and uridine phosphorylase (150 units) were added and the suspension mixed for two days at 37° C. The reaction was filtered and the filtrate lyophilized. The cake was extracted three times with acetone. These filtrates were combined and solvent removed in vacuo. The lyophilized powder was twice extracted with acetone and once extracted with methanol. These filtrates were combined with the extractions with methanol. These filtrates were combined with the extractions from above and solvent removed under vacuum. This powder was dissolved in 150 ml 30% n-PrOH/water (v/v) and chromatographed on a (7.5×90) cm column containing P-2 resin. Fractions containing product were pooled, dried in vacuo, resulting in 1.4 g of analytically pure 7-chloro-3-β-D-ribofuranosyl)-3H-imidazo[4,5-b]pyridine which had an $R_f$ value of 0.25 on cellulose developed in $(NH_4)_2SO_4$:1M NaOAc:i-PrOH (79:19:2). M.p. 198° C.; UV $\lambda_{max}$ nm ($\epsilon \times 10^{-3}$) at pH 1 281, 284, 250; at pH 13, 279, 257; NMR $(Me_2SO-d_6)\delta$ 8.80 (s, 1H, $H_2$), 8.34 (d, 1H, J=5.27, $H_5$), 7.49 (d, 1H, J=5.26, $H_6$), 6.07 (d, 1H, J=5.58, $H_{1'}$), 4.5 (b, 1H, $H_{2'}$), 4.1 (b, 1H, $H_{3'}$), 4.0 (b, 1H, $H_{4'}$), 3.5 (b, 2H, $H_{5'}$).

Anal. $(C_{11}H_{12}ClN_3O_4)$. C, H, N.

b.

7-Anilino-3-β-D-ribofuranosyl)-3H-imidazo[4,5-b]pyridine

Aniline (1.6 g, 17.5 mMol) and 1.0 g (3.5 mMol) 7-chloro-3-β-D-ribofuranosyl-3H-imidazo[4,5-b]pyridine were suspended in 100 mL water and heated at 100° C. oil bath for two days. The oil bath temperature was raised to 130° C. and the reaction was continued for two days, when 2 equivalents of aniline were added. On the tenth day of heating, 5 equivalents of aniline were added and the reaction continued for six hours more. The mixture was concentrated in vacuo to give a dark oil. Chromatography twice on silica gel using $CHCl_3/CH_3OH$ (9:1) gave nearly pure 7-anilino-3-β-D-ribofuranosyl)-3H-imidazo[4,5-b]pyridine. This was crystallized in two batches from methanol. Total yield was 0.307 g, 18%; m.p. 186°-187° C. The NMR, UV and HPLC retention time were identical to the product prepared enzymatically.

Anal. for $C_{17}H_{18}N_4O_4$: C, 59.64; H, 5.30; N, 16.37. Found: C, 59.56; H, 5.31; N, 16.36.

EXAMPLE 9

Salts of 7-anilino-3-β-D-ribofuranosyl-3H-imidazo[4,5-b]pyridine

The following salts were generated from 1.0 g (2.9 mMol) of 7-anilino-3-β-D-ribofuranosyl-3H-imidazo[4,5-b]pyridine dissolved in 300 mL of warm methanol by the addition of 3.0 mMol of the acid indicated. The solution was stirred overnight at ambient temperature under a nitrogen atmosphere. The solvent was removed in vacuo to give a solid which was treated as indicated.

Hydrochloride.2H$_2$O: The acid was added as a 4N solution in dioxane. The pale yellow solid was dried. Yield 1.16 g (2.8 mMol, 96%); m.p. 118°-120° C., dec. at 170° C.

Anal. calcd. for $C_{17}H_{18}N_4O_4.HCl.2H_2O$: C, 49.22; H, 5.59; N, 13.51; Cl, 8.55. Found: C, 49.21; H, 5.58; N, 13.50; Cl, 8.60.

Methane Sulfonic.1.5H$_2$O: The tan solid from the reaction was suspended in ether and isolated by filtration. This was repeated and the product dried. Yield 0.75 g (1.6 mMol, 55.6%) of a very hygroscopic material; m.p. 165° C. dec.

Anal. calcd. for $C_{17}H_{18}N_4O_4.CH_4SO_3.1.5H_2O$: C, 46.45; H, 5.41; N, 12.04; S, 6.89. Found: C, 46.25; H, 5.35; N, 11.91; S, 6.82.

Sulfamic Acid: The pale green solid from the reaction was washed with cold methanol and acetone and dried. Yield 1.12 g (2.5 mMol, 88%); m.p. 160°-162° C.

Anal. calcd. for $C_{17}H_{18}N_4O_4.NH_2SO_3H$: C, 46.46; H, 4.82; N, 15.94; S, 7.30. Found: C, 46.26; H, 4.85; N, 15.85; S, 7.24.

L-(+)-Tartrate: A mixture of 0.1 g (0.29 mMol) of 7-anilino-3-β-D-ribofuranosyl-3H-imidazo[4,5-b]pyridine and 0.044 g (0.29 mMol) of L-(+)-tartaric acid in 250 mL water was warmed at 40° C. until a solution formed. The water was removed in vacuo and the residue taken up in absolute ethanol. A small amount of insoluble material was removed by filtration and the ethanol was removed in vacuo to give 0.055 g of white solid. Yield 38.5%; m.p. (dec.) 194°-195° C.

Anal. calcd. for $C_{17}H_{18}N_4O_4.C_4H_6O_6$: C, 51.22; H, 4.91; N, 11.38. Found: C, 51.19; H, 4.96; N, 11.44.

Di-L-(+)-tartrate.1.2H$_2$O: A mixture of 3.0 g (8.76 mMol) of 7-anilino-3-β-D-ribofuranosyl-3H-imidazo[4,5-b]pyridine and 2.63 g (17.52 mMol) L-(+)-tartaric acid was dissolved in a mixture of 800 mL water and 40 mL ethanol. The resulting solution was taken to dryness by lyophilization over six days. Yield 5 g of white solid, 86%; m.p. 163°-164° C.

Anal. calcd. for $C_{17}H_{18}N_4O_4.2C_4H_6O_6.1.2H_2O$: C, 45.21; H, 4.92; N, 8.44. Found: C, 45.50; H, 4.81; N, 8.15.

EXAMPLE 10

7-Anilino-3-(2',3',5'-O-acetyl-β-D-ribofuranosyl)-3H-imidazo[4,5-b]pyridine

7-Anilino-3-β-D-ribofuranosyl-3H-imidazo[4,5-b]pyridine (5.0 g, 14.5 mMol) was dissolved in 50 mL pyridine and the solution was brought to 0° C. The stirred solution was kept in a nitrogen atmosphere while acetic anhydride (10.8 mL, 114.5 mMol) was added dropwise over a 15 minute period. The whole was stirred at 5° C. for 24 hours. The solution was poured onto 300 mL of ice and water. The aqueous mixture was extracted with 500 mL chloroform and the chloroform fraction was washed twice with 100 mL 20% sodium bicarbonate solution, once with 100 mL water, dried, filtered, and the chloroform evaporated under reduced pressure. Yield 6.0 g, 12.8 mMol, 88%; m.p. 66°-68° C. NMR (DMSO-d6): 8.45 δ (s, 1H, $H_2$); 8.03 (d, 1H, J=5.66 Hz, $H_5$); 6.89 (d, 1H, J=5.75, $H_6$; 6.30 (d, 1H, J=5.38 Hz, $H_{1'}$); 2.13, 2.05, 2.02 (s, 9H, 3CH$_3$).

Anal. calcd. for $C_{23}H_{24}N_4O_7$: C, 58.97; H, 5.16; N, 11.96. Found: C, 58.69; H, 5.21; N, 11.94.

EXAMPLE 11

5,7-Dichloro-3-β-D-ribofuranosyl-3H-imidazo[4,5-b]pyridine 5,7-Dichloro-3H-imidazo[4,5-b]pyridine (0.0053 mole, 1.0 g) and uridine (0.00795 mole, 1.94 g), were suspended in 20 ml potassium phosphate, 0.01M at pH 7 with 0.04% potassium azide. The catalysts, purine nucleoside phosphorylase (1900 units) and uridine phosphorylase (1300 units) were added and the suspension mixed for 10 days at 35° C. The reaction was filtered and the cake dissolved in boiling methanol. After filtering, the volume was doubled with water then reduced to one quarter the volume in vacuo at 40° C. The resulting precipitate was collected by filtration and contained 1.3 g (0.0037 mole) of analytically pure 5,7-Dichloro-3-β-D-ribofuranosyl-3H-imidazo[4,5-b]pyridine. M.p. 156°-158° C.; UV $\lambda_{max}$ nm ($\epsilon \times 10^{-3}$) at pH 1, 10% EtOH, 187(8.2), 256(4.2); at pH 13, 10% EtOH, 289(8.7), 260(5.0); $[\alpha]_D^{20} = -15.6$, (C=0.5, DMF); NMR (MC$_2$SO-d$_6$) δ 8.85 (s, 1H, H$_2$), 7.68 (s, 1H, H$_6$), 5.99 (d, 1H, J=5.49, H$_{1'}$), 5.0 (m, 1H, H$_{2'}$), 4.5 (m, 1H, H$_{3'}$), 4.0 (m, 1H, H$_{4'}$), 3.5 (b, 1H, H$_{5'}$)

Anal. ($C_{11}H_{11}N_3O_4Cl_2 \cdot 1.7H_2O$).C, H, N.

EXAMPLE 12

5,7-Dichloro-3-β-D-ribofuranosyl-3H-imidazo[4,5-b]pyridine 5,7-Dichloro-3H-imidazo[4,5-b]pyridine (5 g, 26.7 mMol) and 1,2,3,5-tetra-O-acetyl-β-D-ribofuranose (8.44 g, 26.7 mMol) were intimately mixed with a mortar and pestle and placed in a 100 mL flask. The flask was placed under a vacuum and immersed in a preheated 155° C. oil bath. After five hours the flask was removed and 50 mL of CHCl$_3$ was added to the cooled contents. Saturated sodium bicarbonate solution was added and the layers were separated. The CHCl$_3$ solution was dried over sodium sulfate, filtered, and reduced to an oil in vacuo. The oil was adsorbed onto silica gel and this was put onto a column of silica gel. Elution with CHCl$_3$/EtOAc (2:1, 1.5 L) and CHCl$_3$/EtOAc (1:1, 1 L) and concentration of the appropriate fractions gave 8.89 g of tri-O-acetylated nucleoside. NMR(DMSO-d6): 8.81 δ (s, 1H, H$_2$); 7.72 (s, 1H, H$_6$); 6.31 (d, 1H, J=5.14 Hz, H$_{1'}$); 2.12, 2.05, 2.00 (s, 9H, 3CH$_3$). Unreacted 5,7-dichloro-3H-imidazo[4,5-b]pyridine (1.09 g, 5.8 mMol) was recovered by chromatography.

A portion of the tri-O-acetylated material (0.8 g, 1.8 mMol) was added to 50 mL of methanol which had been presaturated with ammonia and stirred at ambient temperature for 3 hours. The solvent and excess ammonia were removed in vacuo and the residue was purified by chromatography on silica gel. Elution with CHCl$_3$/CH$_3$OH (9:1), combination of the appropriate fractions, and removal of the solvent gave 0.31 g (1 mMol) of 5,7-dichloro-3-β-D-ribofuranosyl-3H-imidazo[4,5-b]pyridine as the monohydrate; mp 148°-150° C. (lit. 155°-156° C.; B. L. Cline, et al., *J. Heterochem.*, 15, 839-847 (1978); 137°-138° C.; T. Itoh, et al., *Nucleotides and Nucleosides*, 2, 387-397 (1983)); NMR(DMSO-d6): 8.49 δ (s, H$_2$); 7.67 (s, H$_6$); 5.99 (d, H$_{1'}$, J=5.50 Hz).

Anal. calcd. for $C_{11}H_{11}N_3O_4Cl_2 \cdot H_2O$: C, 39.07; H, 3.87; N, 12.43; Cl, 20.97. Found: C, 39.06; H, 3.94; N, 12.36; Cl, 20.97.

EXAMPLE 13

7-Chloro-3H-imidazo[4,5-b]pyridine-4-oxide

7-Chloro-3H-imidazo[4,5-b]pyridine (15 g, 97.7 mMol) was dissolved in 150 mL of glacial acetic acid and m-chloroperbenzoic acid (23 g, 131 mMol) was added in portions to the stirred solution. After 12 hours the solid was isolated and washed with ether. The solid was suspended in 400 mL of hot ethanol, stirred, and isolated. The product, 7-chloro-3H-imidazo[4,5-b]pyridine-4-oxide, was dried in vacuo. Yield 14.98 g (8.83 mMol, 90.4%); m.p. 200° C. (dec).

Anal. calcd. for $C_6H_4ClN_3O$: C, 42.50; H, 2.38; N, 24.78; Cl, 20.91. Found: C, 42.23; H, 2.39; N, 24.70; Cl, 20.73.

EXAMPLE 14

5,7-Dichloro-3H-imidazo[4,5-b]pyridine

7-Chloro-3H-imidazo[4,5-b]pyridine-4-oxide (15 g, 88.5 mMol) and 300 mL phosphorus oxychloride were heated at 110° C. under a nitrogen atmosphere. After 4 hours the excess phosphorus oxychloride was removed in vacuo. The residue was dissolved in water and the solution was neutralized by the addition of aqueous ammonium hydroxide. The suspension was cooled and the solid isolated. After drying, the product, 5,7-dichloro-3H-imidazo[4,5-b]pyridine, weighed 10.5 g (54.5 mMol, 61.6%); m.p. 263° C.; NMR (DMSO-d6): 8.58 δ (s, 1H, H$_2$); 7.58 (s, 1H, H$_5$).

Anal. calcd. for $C_6H_3N_3Cl_2 \cdot 0.25H_2O$: C, 37.43; H, 1.83; N, 21.83; Cl, 36.83. Found: C, 37.39, H, 1.85; N, 21.81; Cl, 36.71.

EXAMPLE 15

7-Anilino-3-β-D-ribofuranosyl)-3H-imidazo[4,5-b]pyridine a. 5-Chloro-7-anilino-3H-imidazo[4,5-b]pyridine 5,7-Dichloro-3H-imidazo[4,5-b]pyridine (4.4 g, 23.3 mMol) was heated with 50 mL of aniline at 135° C. under a nitrogen atmosphere. After 48 hours the reaction mixture was cooled and diluted with 50 mL methanol. The 5-chloro-7-anilino-3H-imidazo[4,5-b]pyridine was isolated and washed with methanol. The dried solid weighed 4.8 g. Yield 19.6 mMol, 84%; m.p. >300° C.; NMR (DMSO-d6): 9.23 δ (s, 1H, NH-anilino); 8.24 (s, 1H, H$_2$); 7.44-7.37 (m, 5H, aromatic); 6.69 (s, 1H, H$_5$).

Anal. calcd. for $C_{12}H_9N_4Cl$: C, 58.91, H, 3.71, N, 22.90; Cl, 14.49. Found: C, 58.87, H, 3.75; N, 22.88; Cl, 14.43.

b. 7-Anilino-5-chloro-3-β-D-ribofuranosyl-3H-imidazo[4,5-b]pyridine

After a crystal of iodine was added to an intimate mixture of 1,2,3,5-tetra-O-acetyl-β-D-ribofuranose (5.2 g, 16 mMol) and 7-anilino-5-chloro-3H-imidazo[4,5-b]pyridine (4.0 g, 16 mMol), the mixture was heated in vacuo at 155° C. After 2 hours, the cooled reaction mixture was suspended in methanol and filtered to remove the unreacted heterocycle (2.29 g). The filtrate was taken to dryness in vacuo and treated with an excess of methanol previously saturated with ammonia. Purification by flash chromatography on silica gel (the residue was adsorbed onto silica gel and placed on the top of the column), elution with chloroform/methanol (20:1 v/v), and removal of the solvent gave 1.22 g (3.2 mMol) of 7-anilino-5-chloro-3-$\beta$-D-ribofuranosyl-3H-imidazo[4,5-b]pyridine; yield 46.8%; m.p. 157°–160° C. UV max (nm) at pH 1, 307 ($\epsilon$15,700); pH 13, 250 sh ($\epsilon$9,900), 300 $\epsilon$19,400); NMR (DMSO-d6): 9.42 d (s, 1H, NH); 8.50 (s, 1H, H$_2$); 7.43–7.12 (m, 5H, Phenyl); 6.71 (s, 1H, H$_5$); 5.93 (d, 1H, J=5.97 Hz, H$_{1'}$).

Anal. calcd. for $C_{17}H_{17}N_4ClO_4$: C, 54.19; H, 4.55; N, 14.87; Cl, 9.41. Found: C, 53.96; H, 4.60; N, 14.82; N, 9.33.

c.
7-Anilino-3-$\beta$-D-ribofuranosyl)-3H-imidazo[4,5-b]pyridine

A solution of 5-chloro-7-anilino-3-$\beta$-D-ribofuranosyl-3H-imidazo[4,5-b]pyridine (0.104 g, 0.28 mMol) in 150 mL of water containing 0.1 g of 10% palladium on carbon was hydrogenated in a Parr apparatus for 120 h at 45 psi. The catalyst was removed by filtration and washed well with water. The aqueous filtrate was taken to dryness in vacuo and the residue recrystallized from a minimum of boiling water to give 13 mg of 7-anilino-3-$\beta$-D-ribofuranosyl-3H-imidazo[4,5-b]pyridine as shown by retention time on reversed phase HPLC and the following: UV max (nm) at pH 1, 304; at pH 13, 301; NMR (DMSO-d6): 9.06 $\delta$ (s, 1H, NH); 8.43 (s, 1H, H$_2$); 7.97 (d, 1H, J=5.66 Hz, H$_5$); 7.40–7.07 (m, 5H, Phenyl); 6.88 (d, 1H, J=5.83 Hz, H$_6$); 5.97 (d, 1H, J=6.32 Hz H$_{1'}$).

Anal. calcd. for $C_{17}H_{18}N_4O_4$: C, 59.64; H, 5.30; N, 16.37. Found: C, 59.37; H, 5.36; N, 16.25.

EXAMPLE 16

Analgesic Activity

Acetic Acid Writhing Test (AAWT)

Using the procedure described by Koster et al. in *Fed. Proc.* 18, 412 (1959) and Vinegar et al. in *Handbook of Experimental Pharmacology*, 50-2, ch. 26, Anti-inflammatory Drugs, Ed. J. R. Vane and S. H. Ferreira (1978), the acetic acid writhing test was performed, using both the mouse and the rat, to demonstrate the mild analgesic activity of the compound of formula (I). Comparative results between Compound A (7-anilino-3-$\beta$-D-ribofuranosyl-3H-imidazo[4,5-b]pyridine) and aspirin, an AACO inhibitor are given in Table I.

New Trypsin Hyperalgesic Assay (NTHA)

A sensitive mild analgesic assay is the New Trypsin Hyperalgesic Assay (NTHA). At the start of the assay 250 $\mu$g of trypsin is injected in one hindlimb of each rat. Thirty minutes later each drug is given per os. One hour after the drugs are given the sensitivity of each rat to a 3.0 kg force is determined. The ED$_{50}$ of a compound is the dose which reduced the average pain score of a group of rats 50% relative to a solvent control group (Table I).

TABLE I

| | ANALGESIC ACTIVITY | | |
|---|---|---|---|
| | ED$_{50}$, mg/kg, p.o. (number of animals, n, exceeds 10) | | |
| Test | Compound A | Aspirin | Acetaminophen |
| AAWT (Mouse) | 0.33 ± 0.038 | 21 ± 3.4 | 216 ± 38.4 |
| AAWT (Rat) | 0.74 ± 0.093 | 137 ± 16.9 | 127 ± 38.4 |
| NTHA (Rat) | 0.10 ± 0.030 | 14 ± 2.7 | 13 ± 1.7 |

EXAMPLE 17

Anti-inflammatory Activity

Carrageenin Pleurisy Assay (CPA)

Following the procedure described by Vinegar et al. in *Proc. Soc. Exp. Biol. Med.* 151, 5546, (1976), the acute anti-inflammatory activity of the Compound A (defined in Example 16, vide supra) was compared with that of known anti-inflammatory drugs, i.e., aspirin an acetaminophen in the rat. The average 3 hour exudate volume for each drug treated group was determined and the % inhibition relative to a solvent control group calculated, the ED$_{50}$ being the dose required to reduce the 3 hour exudate volume by 50%.

TABLE II

| Results of Acute Anti-inflammatory Activity Assay (CPA) All Results Expressed as ED$_{50}$ mg/kg, p.o. (n exceeds 10) | |
|---|---|
| Aspirin | 28 ± 3.2 |
| Acetaminophen | 172 ± 22.4 |
| Compound A | 0.24 ± 0.063 |

EXAMPLE 18

Anti-inflammatory Activity

Antipyretic Activity

The Yeast-induced hyperthermia assay was used according to the procedure described by Khalili-Varasteh et al. in *Arch. Int. Pharmacodyn.* 219, 149–159 (1976) to demonstrate the antipyretic activity of Compound A, vide supra and certain known antipyretics in the rat. The results are shown in Table III.

TABLE III

| Results of Antipyretic Activity Assay Rat Yeast Hyperthermia All results are expressed in ED$_{50}$ mg/kg (p.o.) (n exceeds 10) | | |
|---|---|---|
| Compound A | Aspirin | Acetaminophen |
| 0.65 ± 0.06 | 50 ± 8.1 | 72 ± 8.6 |

EXAMPLE 19

Pharmaceutical Formulations

Compound A is 7-anilino-3-$\beta$-D-ribofuranosyl-3H-imidazo[4,5-b]pyridine

| A. Capsule | |
|---|---|
| Ingredient | Amount per capsule (mg) |
| Compound A | 30.0 |
| Lactose | 174.0 |
| Corn Starch | 174.0 |
| Stearic Acid | 2.0 |

The finely ground active compound is mixed with the powdered excipients lactose, corn starch and stearic acid and packed into gelatin capsule.

| B. Tablet | |
|---|---|
| Ingredient | Amount per tablet (mg) |
| Compound A | 30.0 |
| Lactose | 125.0 |
| Corn Starch | 50.0 |
| Polyvinylpyrrolidone | 3.0 |
| Stearic Acid | 1.0 |
| Magnesium stearate | 1.0 |

The Compound A is finely ground and intimately mixed with the powdered excipients lactose, corn starch, polyvinylpyrrolidone, magnesium stearate and stearic acid. The formulation is then compressed to form one tablet.

| C. Suppository | |
|---|---|
| Ingredient | Amount per suppository (mg) |
| Compound | 100.0 |
| Cocoa Butter, q.s. or Wecobee Base | 2.0 |

Wecobee is the trade name of a hydrogenated carboxylic acid.

EXAMPLE 20

Toxicity

The LD$_{50}$ of Compound A, 7-anilino-3-$\beta$-D-ribofuranosyl-3H-imidazo[4,5-b]pyridine, in Charles River CD rats was found to be greater than 100 mg/kg for males and females. This is well above the therapeutic range.

We claim:

1. A compound of formula (I)

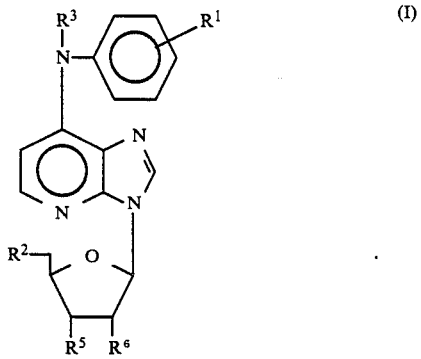

wherein
$R^1$ is hydrogen, halo, C$_{1-4}$ alkyl, trifluoromethyl, C$_{1-4}$ alkoxy or a group of formula COOR$^4$ wherein R$^4$ is hydrogen or C$_{1-4}$ alkyl;
$R^2$, $R^5$ and $R^6$ are the same or different and independently represent hydrogen, halo or hydroxy;
or $R^5$ and $R^6$ also independently represent groups as defined above or groups of formula —OCOR$^7$ in which R$^7$ is hydrogen, C$_{1-4}$ alkyl or phenyl optionally substituted by one or more groups selected from halo, C$_{1-4}$ alkyl and trifluoromethyl;
or R$^2$ also represents a phosphate group or a group of formula —OCOR$^7$ in which R$^7$ is as defined above; and
$R^3$ represents hydrogen, a group of formula COR$^4$ wherein R$^4$ is as defined above, C$_{1-4}$ alkyl or C$_{3-6}$ cycloalkyl;
or a pharmaceutically acceptable salt thereof.

2. A compound of claim 1, wherein R$^1$ represents hydrogen or halo and R$^3$ represents hydrogen, R$^5$ and R$^6$ both represent hydroxy, or a pharmaceutically acceptable salt thereof.

3. A compound of claim 1, wherein R$^1$ represents hydrogen or halo; R$^2$ represents hydrogen, hydroxy or halo; and R$^5$ and R$^6$ are both hydroxy or both groups of formula —OCOR$^7$ wherein R$^7$ represents C$_{1-4}$ alkyl; or a pharmaceutically acceptable salt thereof.

4. A compound selected from:
7-anilino-3-(5-chloro-5-deoxy-$\beta$-D-ribofuranosyl)-3H-imidazo[4,5-b]pyridine;
7-anilino-3-(5-deoxy-$\beta$-D-ribofuranosyl)-3H-imidazo[4,5-b]pyridine; and
7-anilino-3-(5-fluoro-5-deoxy-$\beta$-D-ribofuranosyl)-3H-imidazo[4,5-b]pyridine;
or a pharmaceutically acceptable salt thereof.

5. 7-Anilino-3-$\beta$-D-ribofuranosyl-3H-imidazo[4,5-b]pyridine, or a pharmaceutically acceptable salt thereof.

6. A method of treating pain in a mammal in need thereof which comprises administering to said mammal an effective pain treatment amount of the compound or salt of any one of claims 1, 2, 3 or 4.

7. A method of treating inflammation in a mammal in need thereof which comprises administering to said mammal an effective inflammation treatment amount of the compound or salt of any one of claims 1, 2, 3 or 4.

8. A method of treating fever in a mammal in need thereof which comprises administering to said mammal an effective fever treatment amount of the compound or salt of any one of claims 1, 2, 3 or 4.

9. A method of treating pain in a mammal in need thereof which comprises administering to said mammal an effective pain treatment amount of the compound or salt of claim 5.

10. A method of treating inflamation in a mammal in need thereof which comprises administering to said mammal an effective inflamation treatment amount of the compound or salt of claim 5.

11. A method of treating fever in a mammal in need thereof which comprises administering to said mammal an effective fever treatment amount of the compound or salt of claim 5.

12. A pharmaceutical composition comprising the compound or salt of any one of claims 1, 2, 3 or 4 together with a pharmaceutically acceptable carrier therefore.

13. A pharmaceutical composition comprising the compound or salt of claim 5 together with a pharmaceutically acceptable carrier therefore.

* * * * *